(12) United States Patent
Kjær et al.

(10) Patent No.: US 12,226,495 B2
(45) Date of Patent: Feb. 18, 2025

(54) ¹⁸F-LABELED NOVEL TETRAZINES IMAGING PROBES FOR PRETARGETING IN PET IMAGING

(71) Applicants: Rigshospitalet, Copenhagen Ø (DK); Københavns Universitet, Copenhagen Ø (DK)

(72) Inventors: Andreas Kjær, Copenhagen Ø (DK); Matthias Manfred Herth, Copenhagen Ø (DK); Elsa Johanna Louise Steen, Copenhagen Ø (DK); Jesper Tranekær Jørgensen, Copenhagen Ø (DK); Hannes Mikula, Vienna (AT); Christoph Denk, Vienna (AT)

(73) Assignees: Rigshospitalet, Copenhagen Ø (DK); Københavns Universitet, Copenhagen Ø (DK)

( * ) Notice: Subject to any disclaimer, the term of this patent is extended or adjusted under 35 U.S.C. 154(b) by 646 days.

(21) Appl. No.: 17/612,144

(22) PCT Filed: May 25, 2020

(86) PCT No.: PCT/EP2020/064432
§ 371 (c)(1),
(2) Date: Nov. 17, 2021

(87) PCT Pub. No.: WO2020/239687
PCT Pub. Date: Dec. 3, 2020

(65) Prior Publication Data
US 2022/0249709 A1 Aug. 11, 2022

(30) Foreign Application Priority Data
May 24, 2019 (DK) .............................. PA201900639

(51) Int. Cl.
| | | |
|---|---|---|
| *A61K 51/04* | (2006.01) | |
| *A61P 35/00* | (2006.01) | |
| *C07D 257/08* | (2006.01) | |
| *C07D 401/04* | (2006.01) | |

(52) U.S. Cl.
CPC ........ *A61K 51/0455* (2013.01); *A61K 51/044* (2013.01); *A61K 51/0491* (2013.01); *A61P 35/00* (2018.01); *C07D 257/08* (2013.01); *C07D 401/04* (2013.01); *C07B 2200/05* (2013.01)

(58) Field of Classification Search
CPC .............. A61K 51/0455; A61K 51/044; A61K 51/0491; A61K 51/0495; A61K 51/1063; A61K 51/1093; A61P 35/00; C07D 257/08; C07D 401/04; C07D 401/14; C07B 2200/05; C07K 2317/40; C07K 16/3046; C07H 19/056
See application file for complete search history.

(56) References Cited

FOREIGN PATENT DOCUMENTS

WO 2012/012612 A2 1/2012

OTHER PUBLICATIONS

Denk et al., "Development of a 18F-Labeled Tetrazine with Favorable Pharmacokinetics for Bioorthogonal PET Imaging," Angew. Chem. Int. Ed., 2014, 53:9655-9659.
Maeck et al., "Somatostatin Receptors as Targets for Nuclear Medicine Imaging and Radionuclide Treatment," The Journal of Nuclear Medicine, 2011, 52(6):841-844.
PCT International Search Report for PCT Application No. PCT/EP2020/064432 mailed Jun. 8, 2020 (3 page).
PCT Written Opinion for PCT Application No. PCT/EP2020/064432 mailed Jun. 8, 2020 (6 page).
Rosecker et al., "Cross-Isotropic Bioorthogonal Tools as Molecular Twins for Radiotheranostic Applications," ChemBioChem, 2019, 20:1530-15135.
Anonymous: 23rd International Symposium on Radiopharmaceutical Sciences, Journal of Labelled Compounds and Radiopharmaceuticals, 2019, 62:S5-S122, XP055718752.
Steen et al., "Pretargeting in Nuclear Imaging and Radionuclide Therapy: Improving Efficacy of Theranosticss and Nanomedicines," Biomaterials, 2018, 179:209-245.

*Primary Examiner* — Michael G. Hartley
*Assistant Examiner* — Samantha L Mejias
(74) *Attorney, Agent, or Firm* — Merchant & Gould P.C.

(57) ABSTRACT

Novel ¹⁸F-labelled tetrazines are provided which are highly reactive to be effective in vivo, suitable for pretargeted positron emission tomography (PET) and accessible in radiochemical yields (RCYs) which allow access to ¹⁸F-labeled tetrazines for clinical applications. The ¹⁸F-labelled tetrazines are developed using a Cu-mediated click indirect labelling approach. Only a subset of compounds appeared to be suitable for clinical pretargeted imaging strategies, and a particular compound which includes the use of an ¹⁸F-labelled azide synthon having an azide structure with glucose as the linker and a triazole moiety within the linker, appears to be highly suited for clinical pretargeted imaging purposes.

10 Claims, 7 Drawing Sheets

[18]F-LABELED NOVEL TETRAZINES IMAGING PROBES FOR PRETARGETING IN PET IMAGING

This application is a National Stage Application of PCT/EP2020/064432, filed 25 May 2020, which claims benefit of Serial No. PA201900639, filed 24 May 2019 in Denmark, and which applications are incorporated herein by reference. To the extent appropriate, a claim of priority is made to each of the above disclosed applications.

FIELD OF THE INVENTION

The present invention relates to pretargeting in nuclear imaging. In particular, the invention relates to $^{18}$F-labeled novel tetrazines imaging probes for pretargeting in PET imaging, more particularly pretargeted PET imaging using a dual click $^{18}$F-labeling strategy.

BACKGROUND OF THE INVENTION

Nanomedicines are promising targeting vectors with high specificity for a broad set of diseases including cancer. Monoclonal antibodies (mAbs) in particular have found wide-spread application in numerous fields of medicine, particularly in oncology, where they can provide selective binding and delivery to specific antigens expressed on cancer cells. Companion diagnostics are agents that predict the success of specific treatment form and are especially interesting in targeted radiotherapy where they can assess precisely the maximum tolerated therapeutic dose. This is needed to reach highest treatment efficacy. Due to the size, nanomedicines possess long accumulation and blood clearance time-frames. Typically, mAbs have a long circulation time in the blood stream, spanning in the range from a few days up to weeks. Therefore, they normally have to be labelled with long-lived radionuclides such as iodine-124, zirconium-89, or indium-111, in order to be compatible with the accumulation timeframe. This results in high radiation burden to non-targeted tissue and low imaging contrast, which reduces the diagnostic values of diagnostics labelled with long-lived radioisotopes. Pretargeted strategies separating the accumulation timeframe from the actual imaging process, reduces thereby radiation dose to healthy tissue and increase imaging contrast. A review on this topic is provided in *Biomaterials* 179 (2018) p. 209-245. Pretargeting enables the use of short-lived positron emission tomography (PET) radionuclides such as fluorine-18 ($^{18}$F) with low effective radiation dose values and beneficial radiophysical imaging properties. Pretargeting based on the tetrazine ligation is thereby one of the most promising strategies. Yet, there remains a formidable challenge how to incorporate $^{18}$F into tetrazines, one of the compounds of the tetrazine ligation. This can be exemplified by early attempts on direct $^{18}$F-labeling of tetrazine-derivatives. They have so far been unsuccessful due to the instability of the scaffold under traditionally applied labeling conditions with fluorine-18, i.e. strong nucleophilic bases in combination with high temperatures (J. Nucl Med 2011, 52). In 2014, the first $^{18}$F-labeled tetrazine was reported (Angew Chem Int Edit 2014, 53 (36), 9655-9659). Yet in this case, direct $^{18}$F-fluorination succeeded since the tetrazine was not highly reactive, and hence was more stable to tolerate the aforementioned harsh labelling conditions. These tetrazines cannot be used for pretargeted approaches since their reaction kinetic are too slow.

WO 2012/012612 discloses the general pretargeted strategy using the tetrazine ligation. Labelling of tetrazine moieties did not succeed in suitable yield because of the reasons displayed above. Disclosed tetrazine structures are not suitable for in vivo pretargeted strategies.

It is an object of the present invention to develop novel $^{18}$F-labeled tetrazines which are highly reactive to be effective in vivo, suitable for pretargeted positron emission tomography (PET) and accessible in radiochemical yields (RCYs) which allow access to $^{18}$F-labeled tetrazines for clinical applications.

It is another object of the present invention to provide a method of incorporating $^{18}$F-labeled tetrazines in complex molecules, particularly in monoclonal antibodies modified with trans-cycloctene (TCO), in vivo using bioorthogonal chemistry for pretargeted strategies.

SUMMARY OF THE INVENTION

According to a first aspect of the invention, the above and other objects are solved by the present invention by the provision of a $^{18}$F-labelled tetrazine formed by reacting a tetrazine with a $^{18}$F-labelled azide synthon, in which said tetrazine is a compound according to any of structures 1-6:

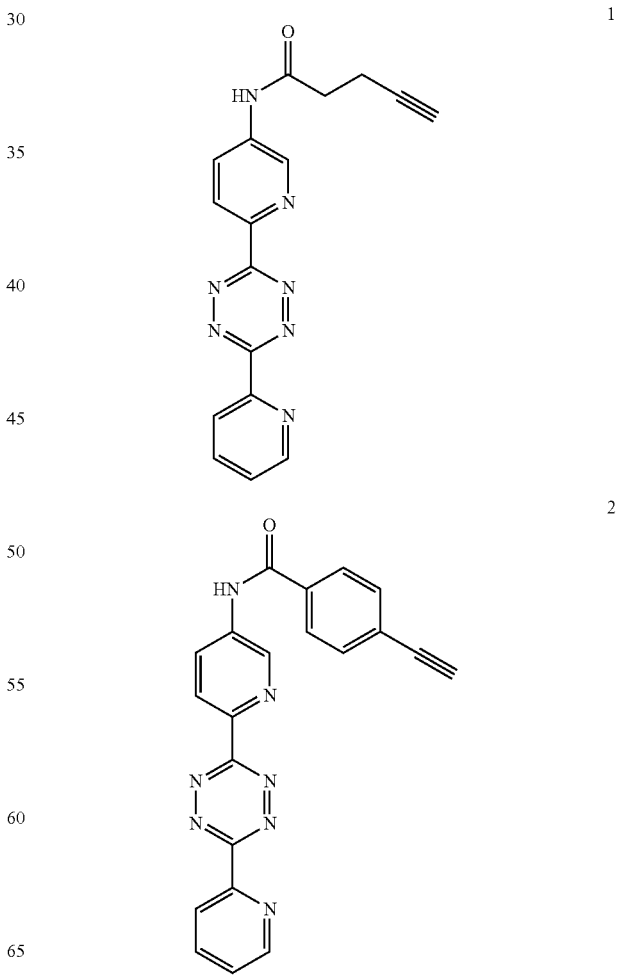

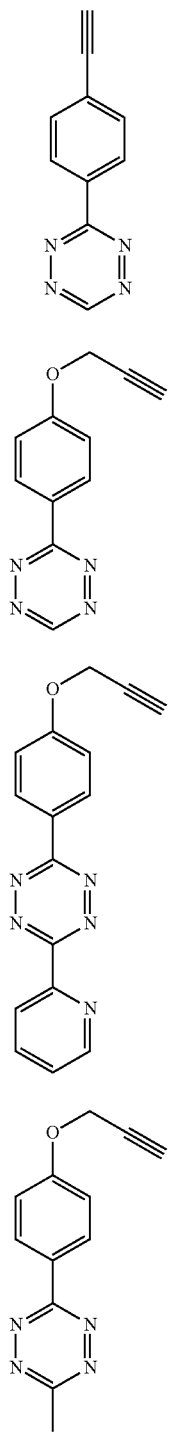

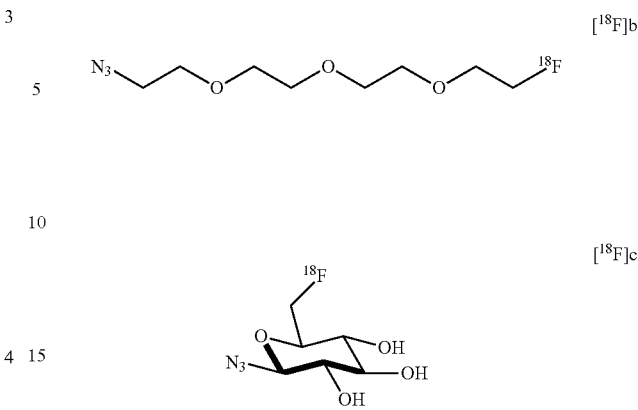

While there is an enormous amount of tetrazines (Tz), hereinafter also referred as tetrazine building blocks, applicants have narrowed the number down to the six compounds above representing high (1-3), medium (4,5) and low reactive tetrazines (6). Likewise, for the $^{18}$F-labelled azide synthon, a group of the three compounds above was selected representing lipophilic (a), medium hydrophilic (b) and strong hydrophilic synthons (c).

Applicants have developed a series of tetrazines, evaluated their potential to be used for pretargeted strategies and $^{18}$F-radiolabeled them ($^{18}$F-labelled tetrazines) using a Cu-mediated click indirect labelling approach. Surprisingly, only a subset of compounds appeared to be suitable for clinical pretargeted imaging strategies. Especially, compound 1c appears to be highly suited for clinical pretargeted imaging purposes.

Hence, in an embodiment of the first aspect of the invention, the tetrazine is a compound according to the structure 1, 3 or 4 and the $^{18}$F-labelled azide synthon is a compound according to the structure $^{18}$F]c.

In other words, in a first aspect the invention may be recited independently as: $^{18}$F-labelled tetrazine formed by reacting a tetrazine with a $^{18}$F-labelled azide synthon, in which said tetrazine is a compound according to any of structures 1, 3 or 4:

and
said $^{18}$F-labelled azide synthon is a compound according to any of structures $^{18}$F]a, $^{18}$F]b, $^{18}$F]c:

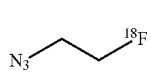

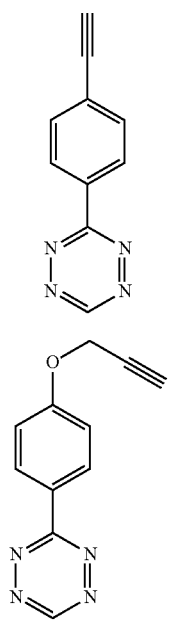

and said $^{18}$F-labelled azide synthon is a compound according to structures [$^{18}$F]c:

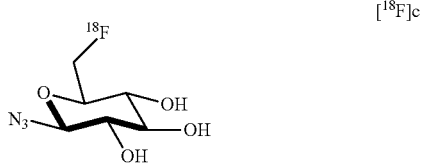

[$^{18}$F]c

These tetrazines show the best results in terms of blocking effect on the normalized tumor uptake, as it shown under the section Detailed description farther below. As mentioned above, especially tetrazine 1c performed outstanding in this blocking test compared to all other compounds. Hence, preferably the tetrazine is a compound according to structure 1 and the $^{18}$F-labelled azide synthon is a compound according to structure [$^{18}$F]c. This tetrazine ("1c") shows by far the best result in terms of normalized tumor uptake and is therefore the best suited for pretargeted PET imaging worldwide using $^{18}$F.

In another embodiment according to the first aspect, said reacting of tetrazine with a $^{18}$F-labelled azide synthon occurs by Cu-catalyzed azide-alkyne [3+2] cycloaddition (CuAAC). The Cu-catalyzed azide-alkyne [3+2] cycloaddition (CuAAC) was identified as the best strategy to access a tetrazine library, since it enables fast and efficient incorporation of fluorine-18 under mild conditions. The library was made up from alkyne-modified tetrazines in combination with $^{18}$F-fluorinated azides.

According to a second aspect of the invention, there is also provided a method of producing an image of an organ in an animal or human, comprising forming in the animal or human a product resulting from the bioorthogonal ligation between i) a $^{18}$F-labelled tetrazine and ii) monoclonal antibodies (mAbs) modified with trans-cyclooctene (TCO).

In an embodiment according to the second aspect, the method is pretargeted immune-positron emission tomography (PET) imaging, by which said monoclonal antibodies (mAbs) modified with trans-cyclooctene (TCO) are provided to accumulate in a target tissue such as a tumor tissue, prior to conducting said biorthogonal ligation with a $^{18}$F-labelled tetrazine. Immuno-positron emission tomography (PET) is the combination of a highly sensitive nuclear imaging technique, PET, and the sharp targeting abilities of radiolabeled mAbs. With immuno-PET, tumor accumulation of mAbs can be detected and quantified. This can then be used in personalized therapeutic approaches, i.e., to guide the selection of patients, who show the highest probability to benefit from such therapy.

Hence, the method is an indirect labelling approach in the form of a dual-click strategy, where the radionuclide (here $^{18}$F) is first introduced into the synthon (here the azide) and reacted with the tetrazine to form a $^{18}$F-labelled tetrazine (so-called click 1). The $^{18}$F-labelled tetrazine is thereafter linked or attached to the nanomedicine, here in the form of monoclonal antibodies (mAbs) modified with trans-cyclooctene (TCO) (so-called click 2). The pretargeted immuno-positron emission tomography (PET) imaging using the bioorthogonal ligation between a radiolabeled tetrazine and monoclonal antibodies (mAbs) modified with trans-cyclooctene (TCO) allows for the use of short-lived radionuclides, here in particular $^{18}$F. In addition, direct $^{18}$F-fluorination of tetrazines can be tedious due to the sensitivity of the tetrazine scaffold. By the invention, a suitable indirect labeling approach is used, by which the combination of different building blocks give access to a library of $^{18}$F-labeled tetrazines with high structural diversity, including reactive structures that have previously proven difficult to access.

In another embodiment according to the second aspect, $^{18}$F-labelled tetrazine is formed by reacting a tetrazine with a $^{18}$F-labelled azide synthon, in which said tetrazine is a compound according to any of structures: 1, 3 or 4, and said $^{18}$F-labelled azide synthon is a compound according to structure [$^{18}$F]c. Preferably, the tetrazine is a compound according to structure 1 and the $^{18}$F-labelled-azide synthon is a compound according to structure [$^{18}$F]c, i.e. compound "1c". As mentioned above, compound "1c" shows the best results in terms of normalized tumor uptake.

In another embodiment according to the second aspect, said reacting of tetrazine with a $^{18}$F-labelled azide synthon occurs by Cu-catalyzed azide-alkyne [3+2] cycloaddition (CuAAC). As mentioned above, the Cu-catalyzed azide-alkyne [3+2] cycloaddition (CuAAC) was identified as a strategy to access a tetrazine library, since it enables fast and efficient incorporation of fluorine-18 under mild condition. CuAAC is well-known in the art and thus at the immediate reach of the skilled person.

In a third aspect, the invention also encompasses the use of a $^{18}$F-labelled tetrazines of the first aspect for imaging accumulation of tumors. The in-vivo effective application of the $^{18}$F-labelled tetrazines, in particular compound "1c" of the invention is unexpected, as one normally would associate performance to be mostly dependent on kinetics. As explained further below, the in vivo tetrazine ligation was not only dependent on the speed kinetics of the respective tetrazine (see Table 1 and FIG. 3). In fact, the linker displayed a key moiety to carry out the tetrazine ligation in vivo and the outcome varied (see FIG. 3).

In a fourth aspect of the invention, the radionuclide $^{18}$F is replaced by either $^{11}$C or $^{68}$Ga. Like $^{18}$F, $^{11}$C and $^{68}$Ga are short-lived radionuclides. While $^{18}$F has a half-life of 110 min, $^{11}$C has a half-life of 20-21 min and $^{68}$Ga a half-life of 68 min.

Any of the embodiments of the first aspect may be used in combination with any of the embodiments of the second or third or fourth aspect.

DETAILED DESCRIPTION

Figure 1:
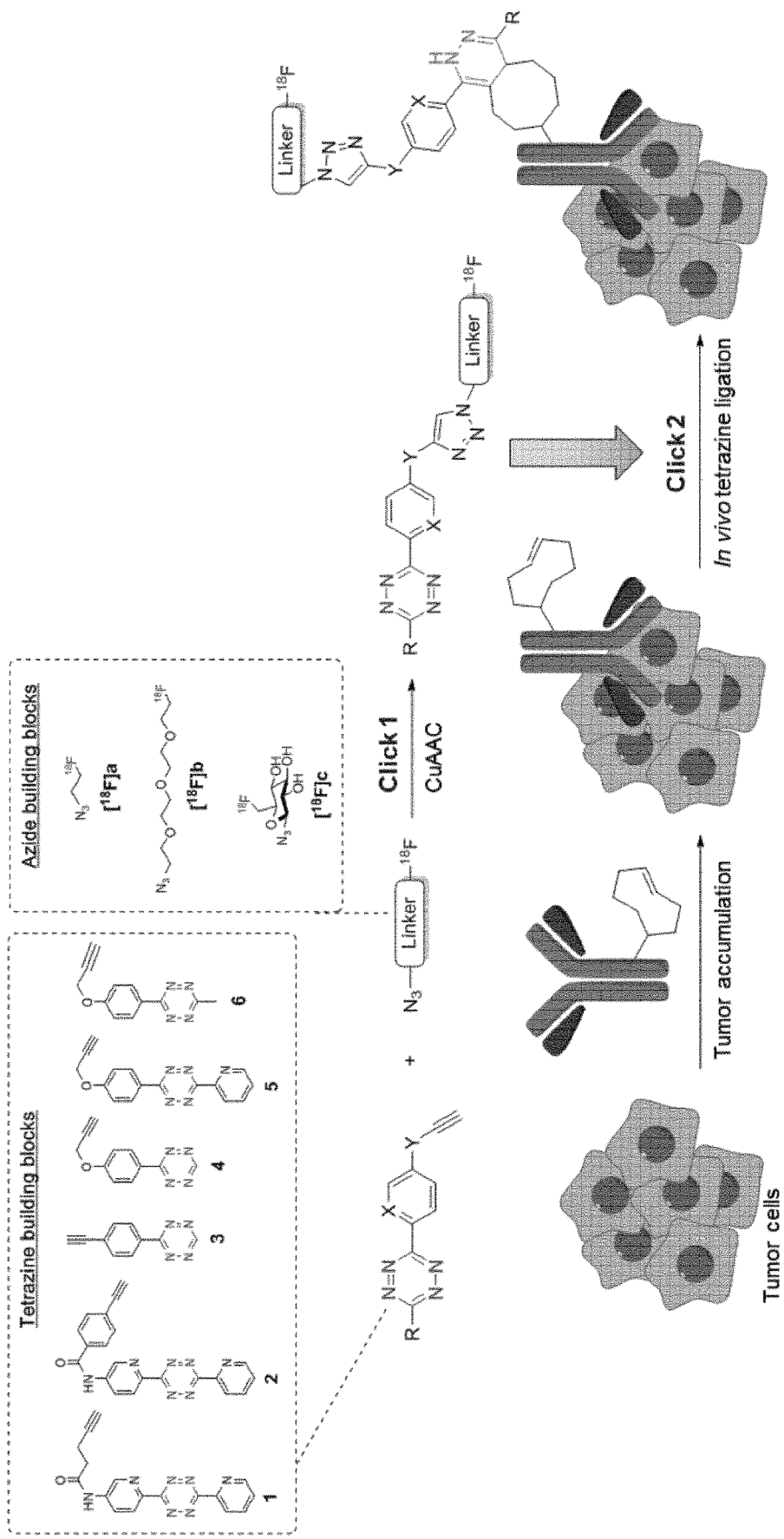
FIG. 1 illustrates the dual-click strategy for the $^{18}$F-labelling of mAbs-TCO (CC49-TCO) in murine colon carcinoma.

The present invention provides a suitable indirect labeling approach, by which the combination of different building blocks would allow access to a library of $^{18}$F-labeled Tz-derivatives with high structural diversity, including reactive structures that have previously proven difficult to access.

The following detailed description explains the design and synthesis of such a library, as well as its evaluation in a newly developed assay for pretargeting, followed by radiolabeling and later evaluation in pretargeted PET imaging studies.

For the design and synthesis of the tetrazine library, applicants set out to find an appropriate reaction that would allow for fast and efficient incorporation of fluorine-18 under mild conditions. A reaction that possesses these features is the Cu-catalyzed azide-alkyne [3+2] cycloaddition (CuAAC). The CuAAC has shown great feasibility as an indirect $^{18}$F-labeling approach for several PET tracers and several synthons functionalized with either an alkyne or azide moiety have been reported.21-25 As such, this reaction was considered to be suitable for the sensitive Tz-scaffold. It was decided to modify the Tz-scaffold with an alkyne and use a $^{18}$F-labeled azido-functionalized synthon. In order to cover a wide spectrum of structural diversity, and thereby be able to study the influence of lipophilicity, metabolic stability and reaction kinetics in the ligation with TCO, six different Tz-scaffolds (1-6) were designed (Table 1). For the azides, a group of three synthons ([$^{18}$F]a-c) was selected (Table 1). Overall, the combination of six Tz-building blocks with three different $^{18}$F-labeled azides offered the possibility to obtain 18 Tz-derivatives with diverse physicochemical properties (Table 1).

TABLE 1

Overview of the Tz-library accessible via CuAAC between different building blocks.

| Building block Combination | Structure R | X | Y | Linker-F | Estimated Rate constant[a] ($M^{-1} s^{-1}$) |
|---|---|---|---|---|---|
| 1a | 2-Pyridyl | N | 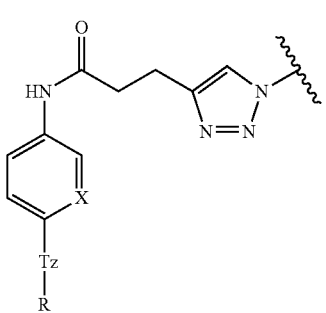 | 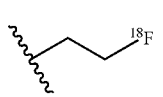 | 230 |
| 1b | 2-Pyridyl | N | 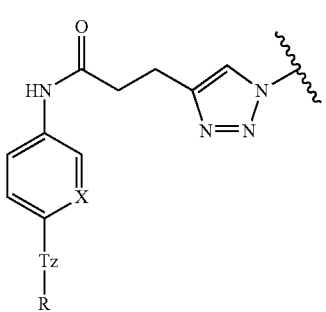 | 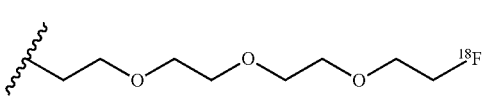 [SMILES: *CCOCCOCCOCC[18F]] | 230 |

TABLE 1-continued

Overview of the Tz-library accessible via CuAAC between different building blocks.

| Building block Combination | Structure R | X | Y | Linker-F | Estimated Rate constant[a] ($M^{-1} s^{-1}$) |
|---|---|---|---|---|---|
| 1c | 2-Pyridyl | N | *amide-linked pyridyl-triazole with propanamide spacer* | *[18F]-fluorodeoxy sugar* | 230 |
| 2a | 2-Pyridyl | N | *benzamide-pyridyl-triazole* | *[18F]-propyl linker* | 230 |
| 2b | 2-Pyridyl | N | *benzamide-pyridyl-triazole* | *[18F]-PEG3 linker* | 230 |
| 2c | 2-Pyridyl | N | *benzamide-pyridyl-triazole* | *[18F]-fluorodeoxy sugar* | 230 |
| 3a | H | C | — | *[18F]-propyl linker* | 204 |
| 3b | H | C | — | *[18F]-PEG3 linker* | 204 |

TABLE 1-continued
Overview of the Tz-library accessible via CuAAC between different building blocks.
| Building block Combination | Structure R | X | Y | Linker-F | Estimated Rate constant[a] ($M^{-1} s^{-1}$) |
|---|---|---|---|---|---|
| 3c | H | C | — | 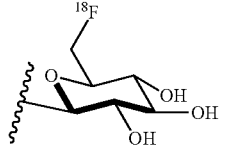 | 204 |
| 4a | H | C | 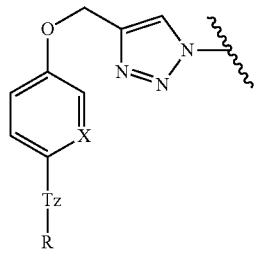 | 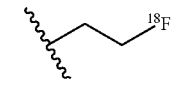 [SMILES: *CC[18F]] | 72 |
| 4b | H | C | 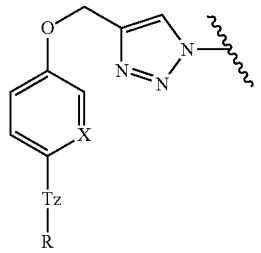 | 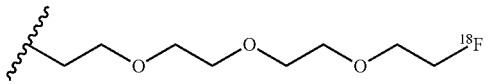 [SMILES: *CCOCCOCCOCC[18F]] | 72 |
| 4c | H | C | 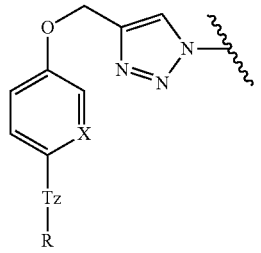 | 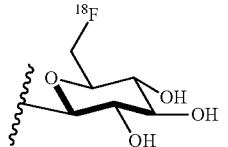 | 72 |
| 5a | 2-Pyridyl | C | 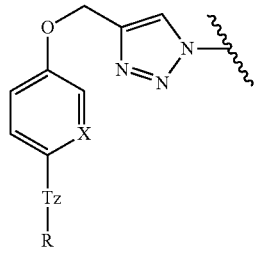 | 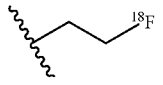 [SMILES: *CC[18F]] | 13 |
| 5b | 2-Pyridyl | C | 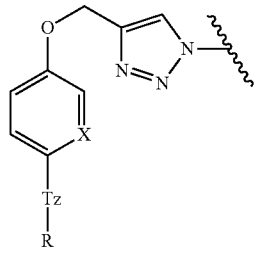 | 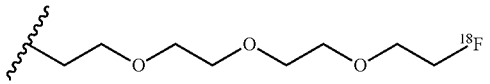 [SMILES: *CCOCCOCCOCC[18F]] | 13 |

TABLE 1-continued

Overview of the Tz-library accessible via CuAAC between different building blocks.

| Building block Combination | Structure R | X | Y | Linker-F | Estimated Rate constant[a] ($M^{-1} s^{-1}$) |
|---|---|---|---|---|---|
| 5c | 2-Pyridyl | C | 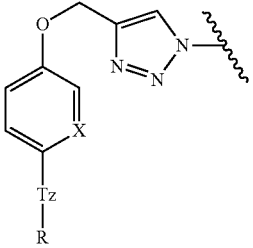 | 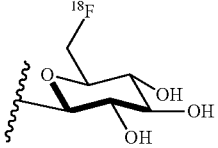 | 13 |
| 6a | Methyl | C | 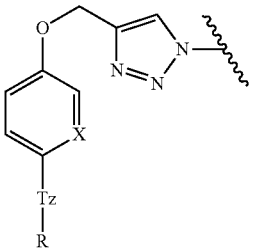 | 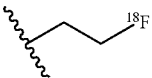 [SMILES: *CC[18F]] | 1.4 |
| 6b | Methyl | C | 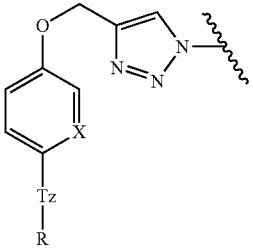 | 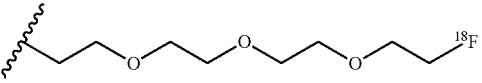 [SMILES: *CCOCCOCCOCC[18F]] | 1.4 |
| 6c | Methyl | C | 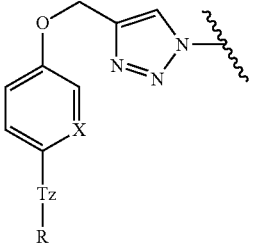 | 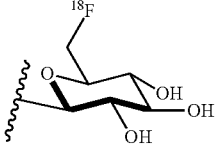 | 1.4 |

Notes:

Second order rate constants are estimated from measurements of the alkyne-Tz building block with TCO at 25° C. in 1,4-dioxane (see supporting information for details)

FIG. 1 shows a dual-click strategy for the $^{18}F$-labeling of CC49-TCO (mAbs modified with TCO) in murine colon carcinoma. The CuAAC was performed between each tetrazine building block and a $^{18}F$-labeled azide synthon (click 1), respectively. The $^{18}F$-labeled click product was injected into tumor bearing mice, where it reacted with CC49-TCO that has accumulated at the tumor-site (click 2).

Figure 2:
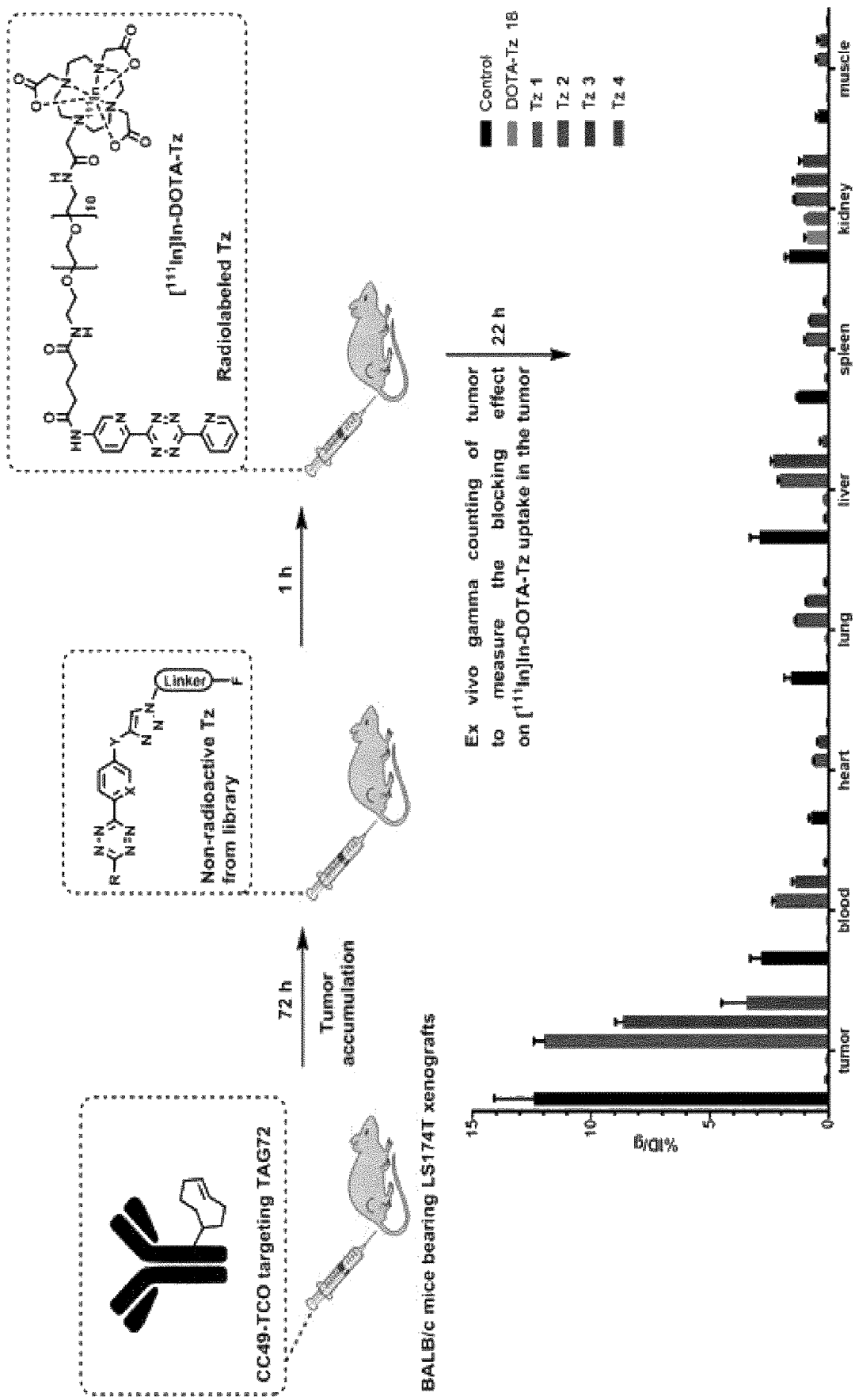
FIG. 2 is a schematic illustration of the blocking assay.

Pretargeted blocking studies: in order to accelerate the screening throughput of potential secondary imaging agents, an assay for pretargeting was established, in which non-radioactive Tz-derivatives were used. This assay was inspired by standard receptor blocking experiments and based on the pretargeted imaging approach reported by Rossin et al. (Angew Chem Int Edit 2010, 49 (19), 3375-3378). In this approach, an $^{111}$In-labeled Tz ([$^{111}$In-DOTA-Tz) was used in pair with CC49-TCO, a non-internalizing mAb, which targets the tumor-associated glycoprotein 72 (TAG72) (Bioconjug Chem 2013, 24 (7), 1210-7.) The set-up for the assay is illustrated in FIG. 2. BALB/c mice bearing LS174T colon carcinoma xenografts were injected intravenously (i.v.) with CC49-TCO (100 µg, 0.67 nmol, ~10 TCOs/mAb) 72 h prior to i.v injection of a non-radioactive Tz (39 nmol/100 μL, 10 equiv with regard to the molar amount of injected [$^{111}$In]In-DOTA-Tz). Two hours after administration of the non-radioactive Tz, the $^{111}$In-labeled Tz (~13 MBq/100 μL, 3.9 nmol) was injected. The animals were euthanized after 22 h and an ex vivo biodistribution study was carried out to assess the potential decrease in tumor uptake of [$^{111}$In]In-DOTA-Tz, which could arise as a result from a blocking effect of the TCO-moieties on the mAb by non-radioactive Tz-derivatives. Control experiments, in which mice were injected only with [$^{111}$In]In-DOTA-Tz were performed to determine the tumor uptake corresponding to 100%. As a positive control for blocking, the non-radioactive precursor of [$^{111}$In]In-DOTA-Tz was used (DOTA-Tz), which blocked ≥98% of the [$^{111}$In]In-DOTA-Tz uptake in the tumor.

FIG. 2 shows the basic methodology of the pretargeted blocking studies.

Figure 3:
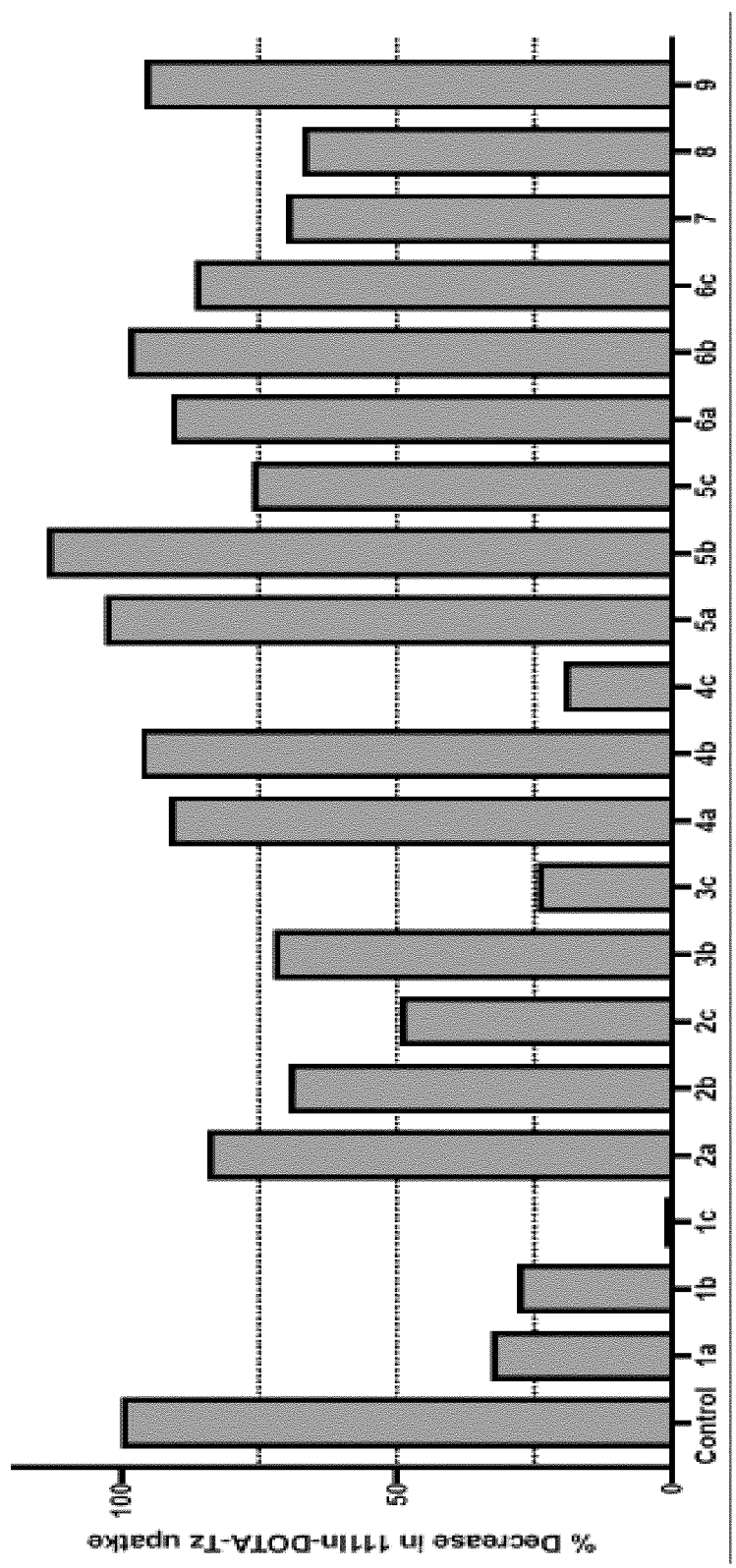
FIG. 3 shows the results of the blocking assay in terms of the blocking effect on the normalized tumor uptake.
Figure 4:
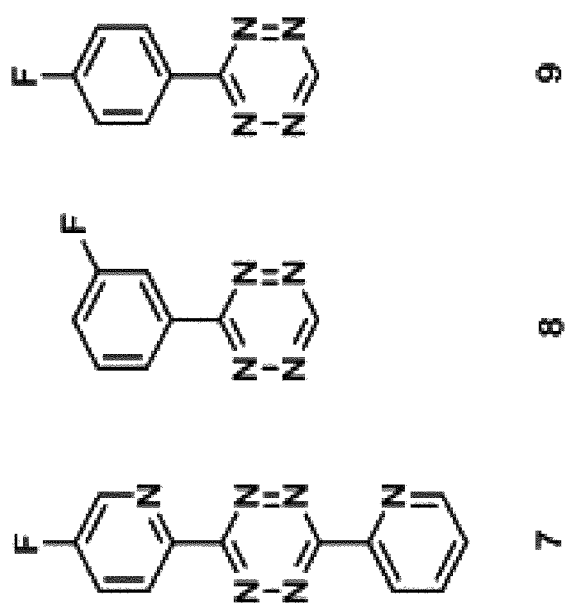
FIG. 4 shows structures for tetrazines 7-12.

FIG. 3 depicts results from blocking assay. The blocking effect on the normalized tumor uptake of [$^{111}$In]In-DOTA-Tz was measured after mice have been pre-administered with non-radiolabeled Tz. Data represent mean±S.E.M. from n=3 in each group. In the bars of the figure, the lower the bar, the better the result. It is seen that the best compound is 1c (tetrazine structure 1 and azide structure [$^{18}$F]c). While 3c and 4c perform relatively well too, but are outperformed by 1c. The azide structure [$^{18}$F]c, having a glucose as the linker and a triazole moiety within the linker (see also N3-linker in FIG. 1), appears to be the only one showing suitable performance. The DOTA-Tz is used as a positive control. In addition to the library presented in this invention, we also compared the performance of tetrazines, which are closely resembling the structures (7-10) in WO 2012/012612. None of these structures showed a good blocking effect. FIG. 4 shows the structures Tz 7-10, the results of which also are included in Table 1.

In conclusion, it is surprising that in vivo tetrazine ligation was not solely dependent on the speed kinetics of the respective tetrazine (see table 1 and FIG. 3). In fact, the linker displayed a key moiety to carry out the tetrazine ligation in vivo and the outcome varied (see FIG. 3). Best results were obtained using a glucose and a triazole moiety within the linker. However and surprisingly, compound 1c performed by far best in the pretargeting assay and reacted with the TCO-moieties at the tumor site in vivo most efficiently. Structural similar cmpds such as 3c performed worse in the blocking experiment.

General Information

Radiochemistry was performed at two different institutes:

Department of Clinical Physiology, Nuclear Medicine & PET, Rigshospitalet, Denmark: [$^{18}$F]Fluoride was produced via the (p,n)-reaction in a cyclotron (60 mikroA CTI Siemens or 40 mikroA Scanditronix) by irradiating [18O]H2O with a 11 MeV (CTI siemens) or 16 MeV (Scanditronix) proton beam. All QMA anion exchange cartridges (Sep-Pak Accell Plus QMA Plus Light, chloride form, Waters) and C18 cartridges (Sep-Pak C18 Plus Short types) were washed with EtOH (20 mL) and water (20 mL) and dried with air before use. Automated syntheses were performed on a Scansys Laboratorieteknik synthesis module housed in a hot cell. Analytical HPLC was performed on a Dionex system connected to a P680A pump, a UVD 170U detector and a Scansys radiodetector. The system was controlled by Chromeleon 6.8 software. Semi-preparative HPLC was performed on the built-in HPLC system in the synthesis module and the flow rate was set to 3 mL/min at all times. Radio-TLC was carried out on same plates as described for the organic chemistry. The fraction of radioactivity on the plates was measured with an instant imager from Packard and analyzed by Optiquant software.

General Procedure for the Preparation of Anhydrous [$^{18}$F] Fluoride for Radiolabeling (Scansys Module):

Irradiated [18O]water containing [$^{18}$F]F— was passed through an anion exchange resin cartridge (Sep-Pak Accell Plus QMA Plus Light, chloride form). [$^{18}$F]Fluoride trapped on the QMA was then eluted with 1 mL of a Kryptofix222/K2CO3 solution (4,7,13,16,21,24-hexaoxa-1,10-diazabicyclo[8.8.8]hexacosane (330 mg), K2CO3 (100 mg) and water (0.8 mL) in MeOH (19.2 mL)) into a 4 mL glass vial. The resulting mixture was then gently concentrated to dryness at 90-110° C. via azeotropic drying using 2× MeCN (1 mL) and a stream of helium. The procedure took 25-30 min and yielded in the ready to react [$^{18}$F]]FK-K222 complex.

(2R,3R,4S,5S,6S)-2-Azido-6-([$^{18}$F]fluoromethyl) tetrahydro-2H-pyran-3,4,5-triol ([$^{18}$F]c)

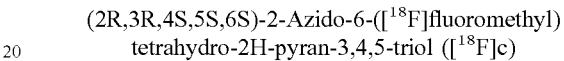

[$^{18}$F]Fluoride was dried according to the general procedures described above. To the dried residue containing [$^{18}$F]F—, precursor 22 (11 mg, 21 μmol) in dry MeCN (500 μL) was added. The mixture was heated at 100° C. for 7 min, thereafter cooled with air for 5 min, before it was diluted with DMSO:water (1:1, 2 mL) for purification by semi-preparative HPLC. The latter was performed on a Luna 5μ C18(2) (100 Å 250×10 mm) column using MeCN (40%) in aqueous phosphate buffer (10 mM, pH 6) as eluent. The collected HPLC fraction was trapped on a Sep-Pak C18 plus cartridge, which was washed with water (5 mL), followed by aqueous 2 M NaOH (1 mL). On-cartridge deprotection was commenced for 60 seconds and the product was eluted with water (2 mL) into a vial containing AcOH (150 μL) to afford [$^{18}$F]c in 19% RCY d.c. to the starting amount of activity, a RCP of ≥99%.

The following CuAAC was performed as following: an aqueous solution of CuSO4.5H2O (16 μL, 100 mg/mL) was mixed with an aqueous solution of sodium ascorbate (16 μL, 300 mg/mL), when the color of the mixture turned yellow a solution of BPDS (80 μL, 50 mg/mL) in water was added. The resulting blue/green mixture was added to a solution of the Tz precursor (~1 mg) in DMF (100 μL). This mixture was then added to the isolated [$^{18}$F]c. The mixture was stirred at 120° C. for 1-5 min.

Figure 5:
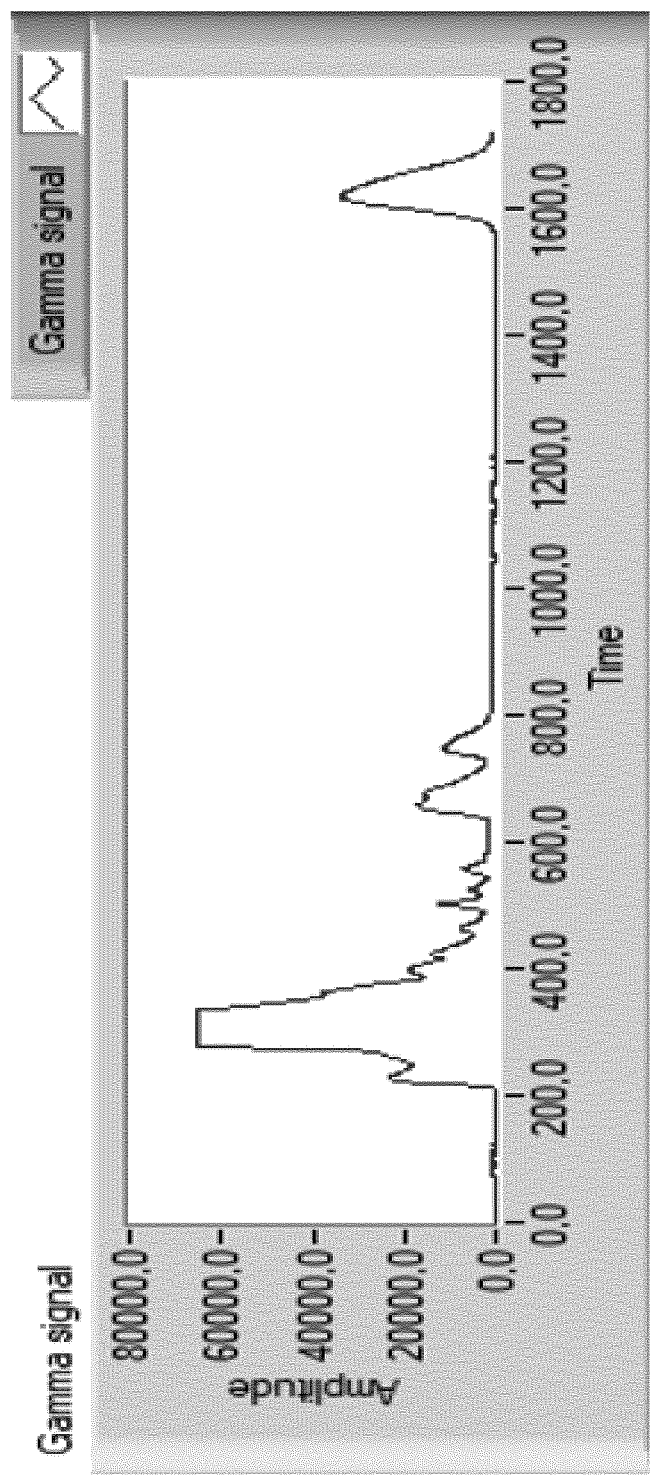
FIG. 5 shows a semi-preparative HPLC chromatogram for [$^{18}$F]c ((Rt=1600 sec) on a Luna 5μ C18(2) (100 Å 250×10 mm) column.
Figure 6A:
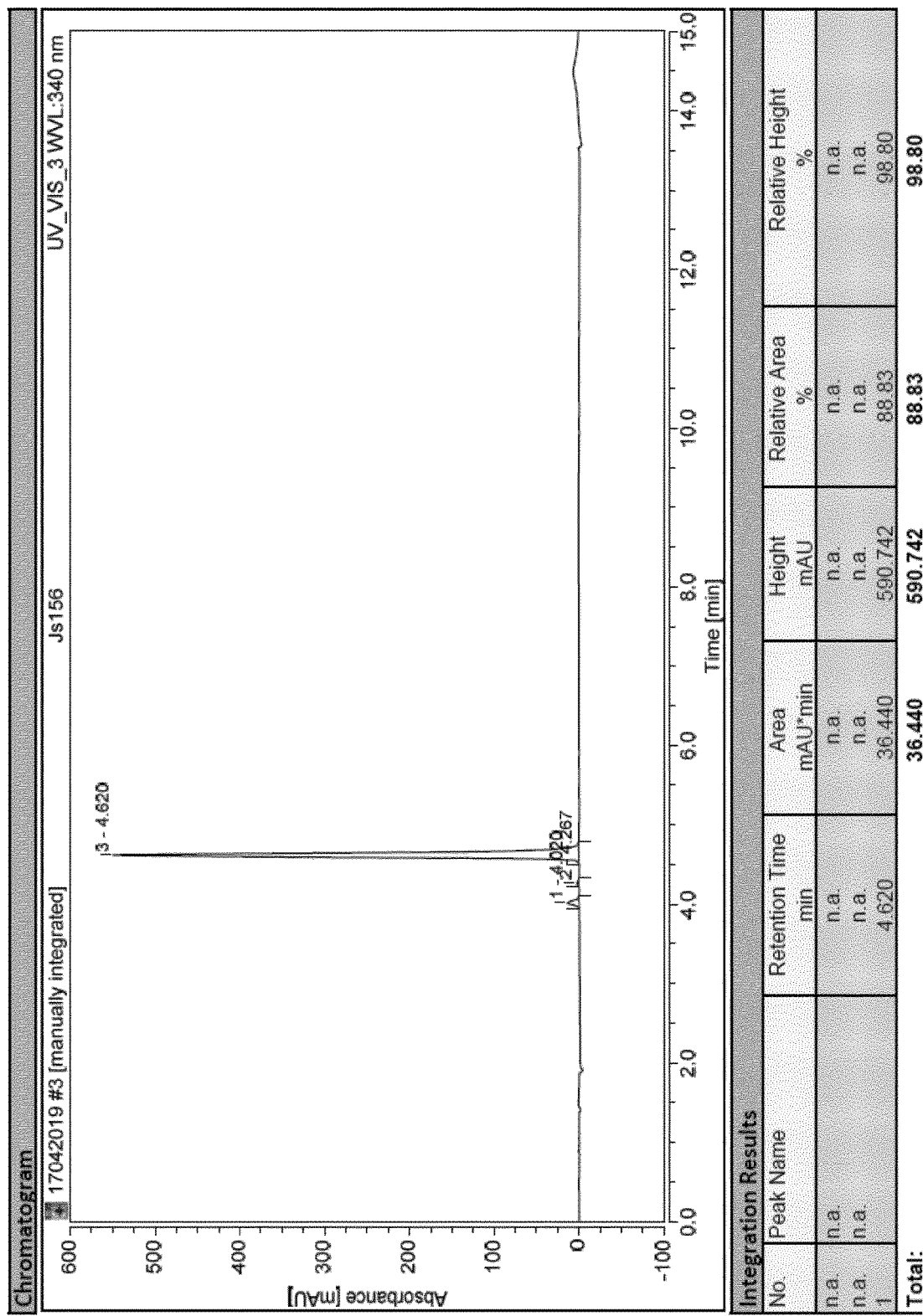
FIG. 6 shows analytical HPLC chromatogram for [$^{18}$F]c (Rt=1600 sec) on a Luna 5μ C18(2) (100 Å 250×10 mm) column.
Figure 6B:
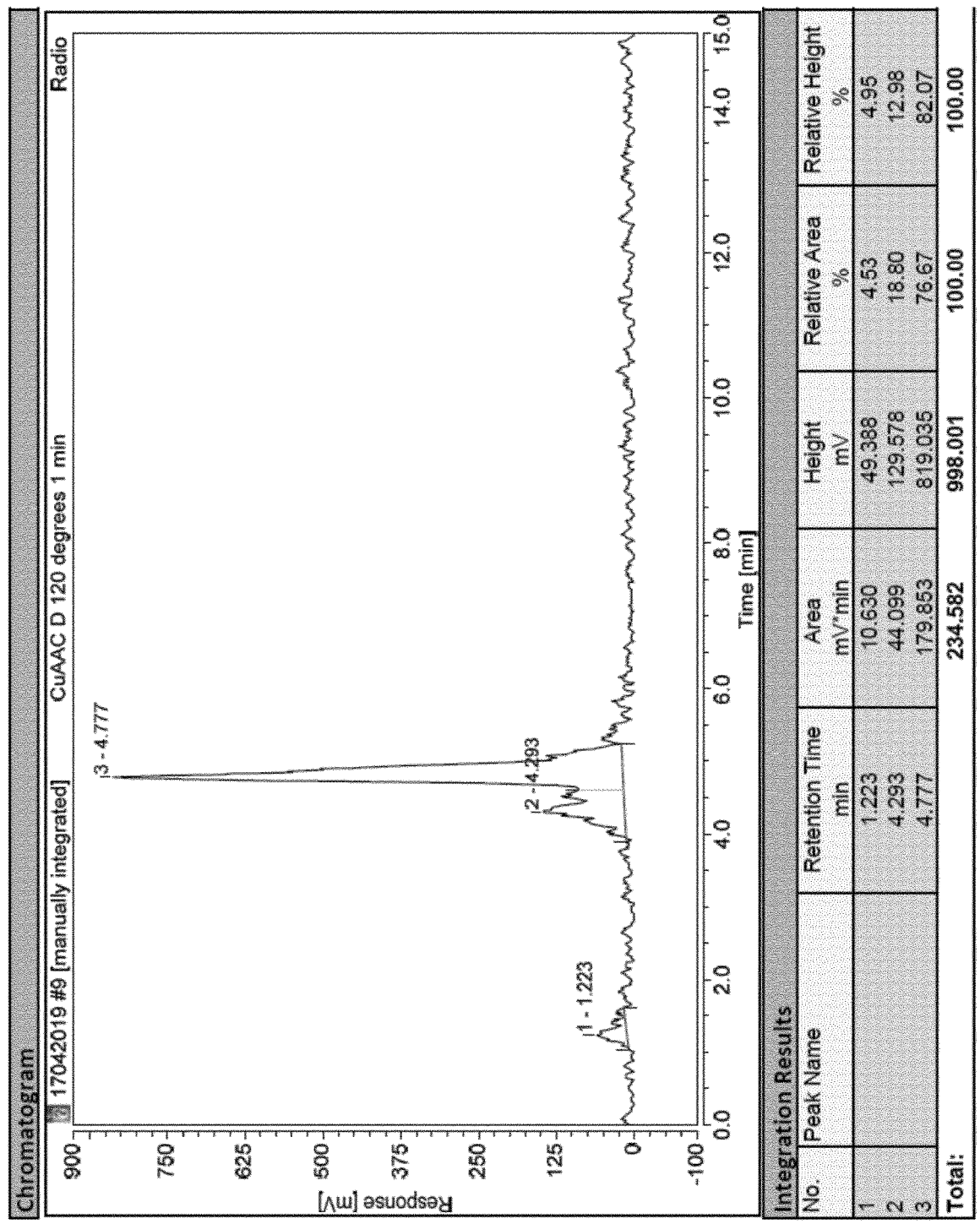

FIG. 5 shows the preparative HPLC chromatogram and FIG. 6 shows an analytical HPLC diagram identifying [$^{18}$F]c.

Applicants have thus developed a small library of $^{18}$F-labeled Tz-derivatives, which was accessible by combining different $^{18}$F-labeled azide synthons with alkyne-functionalized Tz-derivatives via the CuAAC. With this approach Tz-derivatives with high structural diversity. Surprisingly, the in vivo tetrazine ligation was not only dependent on the speed kinetics of the respective tetrazine (see table 1 and FIG. 3). In fact, the linker displayed a key moiety to carry out the tetrazine ligation in vivo and the outcome varied (see FIG. 3). Best results were obtained using a glucose as the linker and a triazole moiety within the linker (N3-linker in FIG. 1). However and surprisingly, compound 1c performed by far best in the pretargeting assay and reacted with the TCO-moieties at the tumor site in vivo most efficiently.

The invention claimed is:

1. A [18F]-labelled tetrazine formed by reacting a tetrazine with a [18F]-labelled azide synthon, in which
said tetrazine is a compound according to any of structures 1-6:

1
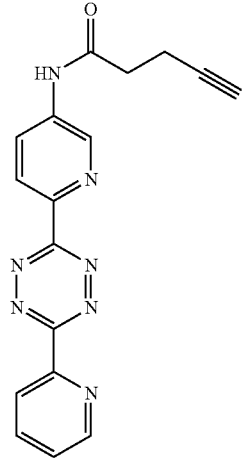

2
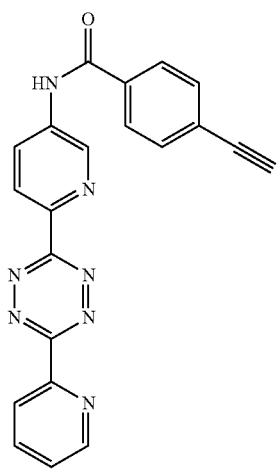

3
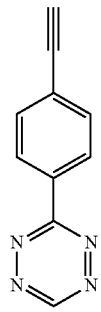

4
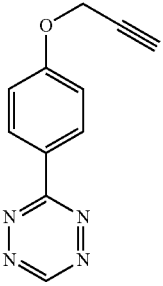

5
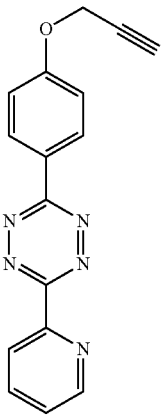

6
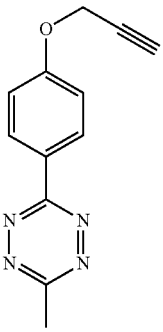

and
said [18F]-labelled azide synthon is a compound according to structures [18F]c:

[18F]a
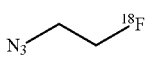

[18F]b
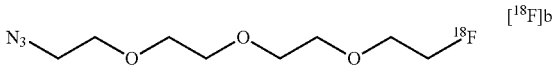

[18F]c
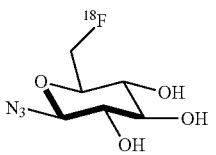

2. The [18F]-labelled tetrazine according to claim 1, wherein the tetrazine is a compound according to any one of structures 1, 3, or 4.

3. The $^{18}$F-labelled tetrazine according to claim 1, wherein said reacting of tetrazine with a $^{18}$F-labelled azide synthon occurs by Cu-catalyzed azide-alkyne [3+2] cycloaddition (CuAAC).

4. A method of producing an image of an organ in an animal or human, comprising forming in the animal or human a product resulting from the biorthogonal ligation between i) the $^{18}$F-labelled tetrazine according to claim 1, wherein said reacting of the tetrazine with the $^{18}$F-labelled azide synthon occurs by Cu-catalyzed azide-alkyne [3+2] cycloaddition (CuAAC), and ii) monoclonal antibodies (mAbs) modified with trans-cyclooctene (TCO).

5. The method according to claim 4, wherein the method comprises pretargeted immune-positron emission tomography (PET) imaging, by which said monoclonal antibodies (mAbs) modified with trans-cyclooctene (TCO) are provided to accumulate in a target tissue prior to conducting said biorthogonal ligation with the $^{18}$F-labelled tetrazine.

6. The method according to claim 4, wherein the $^{18}$F-labelled tetrazine is formed by reacting the tetrazine with the $^{18}$F-labelled azide synthon, in which said tetrazine is a compound according to any one of structures: 1, 3, or 4.

7. The $^{18}$F-labelled tetrazine according to claim 1 for imaging the accumulation of tumors.

8. The $^{18}$F-labelled tetrazine according to claim 2, wherein the tetrazine is a compound according to structure 1.

9. The method according to claim 6, wherein the tetrazine is a compound according to structure 1.

10. The method according to claim 5, wherein the target tissue is a tumor tissue.

\* \* \* \* \*